(12) United States Patent
Ubach et al.

(10) Patent No.: US 11,963,733 B2
(45) Date of Patent: Apr. 23, 2024

(54) CONNECTOR ASSEMBLIES FOR CONNECTING A ROBOTIC ARM WITH A MEDICAL END EFFECTOR

(71) Applicant: NuVasive, Inc., San Diego, CA (US)

(72) Inventors: Antonio Ubach, Tuscon, AZ (US); John C. Love, San Diego, CA (US); Cara Lee Coad, Longmont, CO (US)

(73) Assignee: Nuvasive Inc., San Diego, CA (US)

( * ) Notice: Subject to any disclaimer, the term of this patent is extended or adjusted under 35 U.S.C. 154(b) by 230 days.

(21) Appl. No.: 17/539,587

(22) Filed: Dec. 1, 2021

(65) Prior Publication Data

US 2023/0165651 A1     Jun. 1, 2023

(51) Int. Cl.
| | | |
|---|---|---|
| A61B 34/00 | (2016.01) | |
| A61B 17/70 | (2006.01) | |
| A61B 34/30 | (2016.01) | |
| B25J 9/10 | (2006.01) | |
| A61B 17/00 | (2006.01) | |

(52) U.S. Cl.
CPC .............. *A61B 34/71* (2016.02); *A61B 17/70* (2013.01); *A61B 34/30* (2016.02); *B25J 9/1035* (2013.01); *A61B 2017/00486* (2013.01)

(58) Field of Classification Search
CPC ......... A61B 34/71; A61B 34/30; A61B 17/70; A61B 2017/00486; B25J 9/1035
USPC ............................................................ 606/1
See application file for complete search history.

(56) References Cited

U.S. PATENT DOCUMENTS

| | | |
|---|---|---|
| 6,752,037 B1 | 6/2004 | Miyazawa |
| 7,699,855 B2 | 4/2010 | Anderson et al. |
| 7,886,743 B2 | 2/2011 | Cooper et al. |
| 8,005,570 B2 | 8/2011 | Gloden et al. |
| 8,209,840 B2 | 7/2012 | Norton |
| 8,220,468 B2 | 7/2012 | Cooper et al. |
| 8,533,930 B2 | 9/2013 | Norton |
| 8,746,252 B2 | 6/2014 | McGrogan et al. |
| 9,724,830 B2 | 8/2017 | Norton et al. |
| 10,047,908 B1 | 8/2018 | Bohle, II et al. |

(Continued)

FOREIGN PATENT DOCUMENTS

| | | |
|---|---|---|
| WO | 2014163787 A1 | 10/2014 |
| WO | 2018065490 A2 | 4/2018 |

(Continued)

OTHER PUBLICATIONS

International Search Report and Written Opinion dated Mar. 23, 2023 for International Application No. PCT/US2022/051349.

(Continued)

*Primary Examiner* — Aaron F Roane

(57) ABSTRACT

Connector assemblies for connecting a robotic arm with a medical end effector are disclosed. An example apparatus for connecting a robotic arm with a medical end effector may include a connector housing. An actuation mechanism may be disposed within the connector housing. The actuation mechanism may include a plurality of linkage members and a gear assembly coupled to the linkage members. Each of the plurality of linkage members may be configured to shift between a locked configuration and an unlocked configuration. At least one of the plurality of linkage members may include a first linkage member having an end region. A roller member may be disposed adjacent to the end region of the first linkage member. An actuator may be coupled to the actuation mechanism.

15 Claims, 12 Drawing Sheets

(56) References Cited

U.S. PATENT DOCUMENTS

| | | |
|---|---|---|
| 10,661,449 B2 | 5/2020 | Zachary et al. |
| 11,045,179 B2 | 6/2021 | Troxell et al. |
| 11,096,754 B2 | 8/2021 | Soto et al. |
| 11,154,993 B2 | 10/2021 | Geary |
| 2010/0312247 A1 | 12/2010 | Tuma |
| 2016/0242849 A9 | 8/2016 | Crawford et al. |
| 2019/0021800 A1 | 1/2019 | Crawford et al. |
| 2019/0090966 A1 | 3/2019 | Kang et al. |
| 2019/0388179 A1 | 12/2019 | Krinninger et al. |
| 2021/0039262 A1 | 2/2021 | Maillet et al. |
| 2021/0059774 A1 | 3/2021 | Bar et al. |
| 2022/0031410 A1 | 2/2022 | Ebbitt et al. |
| 2022/0087663 A1 | 3/2022 | Krinninger et al. |

FOREIGN PATENT DOCUMENTS

| | | |
|---|---|---|
| WO | 2018146463 A2 | 8/2018 |
| WO | 2018183212 A1 | 10/2018 |
| WO | 2021222701 A1 | 11/2021 |
| WO | 20211222701 A1 | 11/2021 |
| WO | 2023102012 A1 | 6/2023 |

OTHER PUBLICATIONS

International Search Report and Written Opinion, PCT Application No. PCT/US2022/051349 dated Mar. 23, 2023, 18 pages.

CONNECTOR ASSEMBLIES FOR CONNECTING A ROBOTIC ARM WITH A MEDICAL END EFFECTOR

TECHNICAL FIELD

The present disclosure pertains to surgical medical devices. More particularly, the present disclosure pertains to connectors for connecting a robotic arm with a medical end effector.

BACKGROUND

There are a wide variety of surgical medical devices. Some of these devices include robotic arms, surgical end effectors, and the like. Of the known surgical medical devices, each has certain advantages and disadvantages. There is an ongoing need to provide alternative surgical medical devices.

BRIEF SUMMARY

This disclosure provides design, material, manufacturing method, and use alternatives for medical devices. An apparatus for connecting a robotic arm with a medical end effector is disclosed. The apparatus comprises: a connector housing; an actuation mechanism disposed within the connector housing, the actuation mechanism including a plurality of linkage members and a gear assembly coupled to the linkage members; wherein each of the plurality of linkage members are configured to shift between a locked configuration and an unlocked configuration; wherein at least one of the plurality of linkage members includes a first linkage member having an end region; wherein a roller member is disposed adjacent to the end region of the first linkage member; an actuator coupled to the actuation mechanism, the actuator being configured to shift the plurality of linkage members between the locked configuration and the unlocked configuration; and an adapter coupled to the connector housing, the adapter including a plurality of alignment regions.

Alternatively or additionally to any of the embodiments herein, the actuator includes a button coupled to a rack.

Alternatively or additionally to any of the embodiments herein, the gear assembly includes a pinion engaged with the rack.

Alternatively or additionally to any of the embodiments herein, the pinion is coupled to a drive gear.

Alternatively or additionally to any of the embodiments herein, the drive gear is coupled to one or more gear train rotating gears.

Alternatively or additionally to any of the embodiments herein, the one or more gear train rotating gears are coupled to a geared region of a gear train.

Alternatively or additionally to any of the embodiments herein, further comprising a cam plate having a gear train engaging member coupled to the gear train.

Alternatively or additionally to any of the embodiments herein, the gear train engaging member is configured to allow the cam plate to pivot relative to the gear train.

Alternatively or additionally to any of the embodiments herein, the gear train engaging member includes a geometric end region with a rounded surface.

Alternatively or additionally to any of the embodiments herein, the connector housing is configured to be coupled to a robotic arm.

Alternatively or additionally to any of the embodiments herein, the adapter is configured to be coupled to an end effector adapter.

Alternatively or additionally to any of the embodiments herein, the end effector adapter is coupled to the medical surgical end effector.

Alternatively or additionally to any of the embodiments herein, the end effector adapter includes a plurality of alignment members configured to engage the alignment regions of the adapter.

Alternatively or additionally to any of the embodiments herein, the end effector adapter includes a plurality of linkage receiving regions configured to house the plurality of linkage members when the linkage members are in the locked configuration.

Alternatively or additionally to any of the embodiments herein, further comprising a sterile barrier member disposed between the adapter and the end effector adapter.

Alternatively or additionally to any of the embodiments herein, further comprising a sensor disposed adjacent to the connector housing.

An apparatus for connecting a robotic arm with a medical end effector is disclosed. The apparatus comprises: a connector housing coupled to a robotic arm; an adapter coupled to the connector housing, the adapter being configured to engage an end effector adapter coupled to a surgical end effector; a cam and linkage actuation mechanism coupled to the connector housing, the cam and linkage actuation mechanism including a plurality of linkage members and a cam plate pivotably coupled to a gear train; wherein the plurality of linkage members are configured to shift between a locked configuration and an unlocked configuration; and an actuator coupled to the cam and linkage actuation mechanism, the actuator being configured to shift the plurality of linkage member between the locked configuration and the unlocked configuration.

A method is disclosed. The method comprises: engaging an adapter coupled to a robotic arm with an end effector adapter coupled to a surgical end effector; wherein a connector housing is coupled to the adapter; wherein a cam and linkage actuation mechanism is coupled to the connector housing, the cam and linkage actuation mechanism including a plurality of linkage members and a cam plate pivotably coupled to a gear train; wherein the plurality of linkage members are configured to shift between a locked configuration and an unlocked configuration; wherein an actuator is coupled to the cam and linkage actuation mechanism; and actuating the actuator to shift the plurality of linkage members from the unlocked configuration to the locked configuration and to secure the adapter to the end effector adapter.

Alternatively or additionally to any of the embodiments herein, further comprising disposing a region of a sterile barrier lacking a barrier adapter between the adapter and the end effector adapter.

Alternatively or additionally to any of the embodiments herein, actuating the actuator causes each of the linkage members to engage a linkage member receiving region of the end effector adapter.

Alternatively or additionally to any of the embodiments herein, further comprising: after actuating the actuator, performing a spinal fusion procedure with the robotic arm, the surgical end effector, or both.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
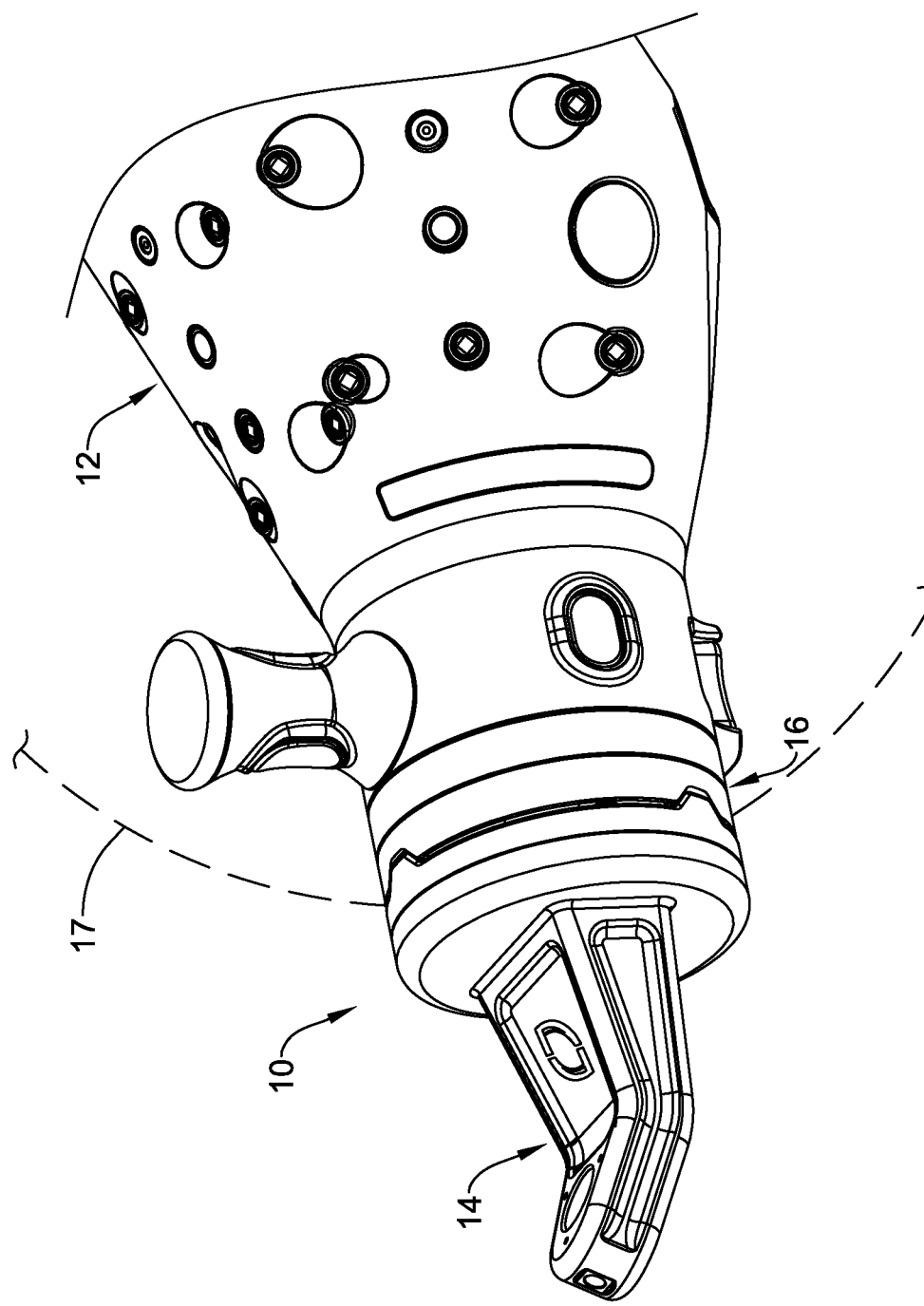
FIG. 1 is a perspective view of a portion of an example surgical system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

A number of medical procedures, such as spinal surgeries, utilize robotic structures and/or tools that can be manipulated by robotic arms. Such robotic structures may include robotic arms with a connector that allows for tools (e.g., tools suitable for a given intervention) to be attached to the robotic arm. It can be appreciated that a medical procedure may need to utilize a number of different tools in conjunction with the robotic arm. Doing so may necessitate swapping out of various tools at different times during the procedure. Disclosed herein are connectors (e.g., connector assemblies) that can be used with various robotic structures. Such connectors may allow for relatively quick and efficient connection/disconnection of tools and/or provide other benefits as disclosed herein.

FIG. 1 is a perspective view of a portion of an example surgical system 10. The system 10 may include a robotic arm 12, a surgical tool and/or medical end effector 14, and a connector assembly 16. In some instances, a sterile barrier 17 (e.g., shown schematically) may be disposed between the robotic arm 12 and the medical end effector 14. In this drawing, only a portion of the robotic arm 12 is shown (e.g., the robot array). It can be appreciated that a variety of different forms and arrangements of robotic arms 12 and/or structures associated with robotic arms are contemplated for use with the surgical system 10. Similarly, in this drawing the medical end effector 14 is depicted as a surgical tool holder or guide. Again, a variety of different forms and arrangements of medical end effectors 14 are contemplated for use with the surgical system 10. It can be appreciated that the term "medical end effector" may be used to generally refer to any one of a number of components including a tool holder, an end effector, an implement, a tool (e.g., a drill, screwdriver, etc.), combinations thereof, and/or the like. In general, the connector assembly 16 is designed to allow for the robotic arm 12 to be securely and efficiently connected to the medical end effector 14. Moreover, the connector assembly 16 is designed so that the medical end effector 14 can be easily and efficiently disconnected from the robotic arm 12, for example when it is desired to swap out the medical end effector 14 for a different medical end effector 14. Concomitantly achieving an easy and secure connection (particularly while safely sandwiching a drape) can be challenging. Examples described herein can address one or more of these challenges.

Figure 2:
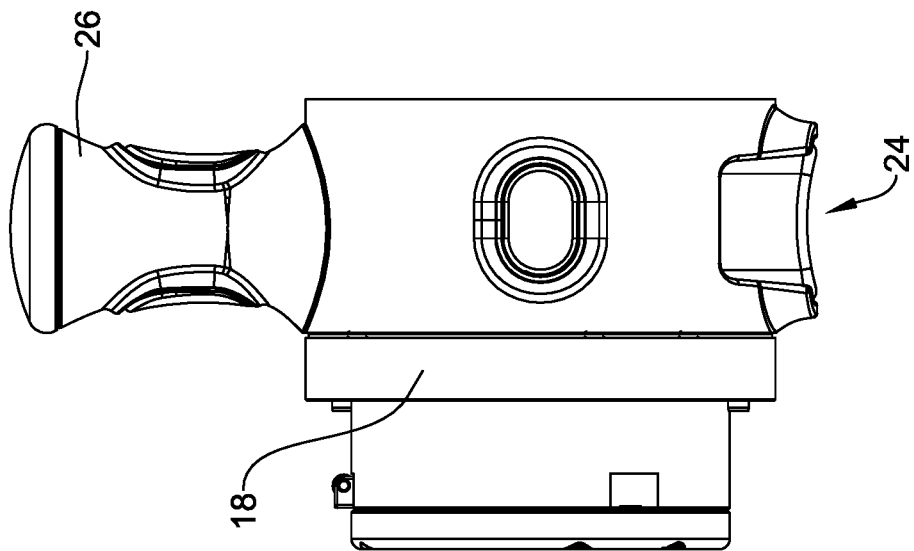
FIG. 2 is an exploded view of an example connector assembly.
Figure 2:
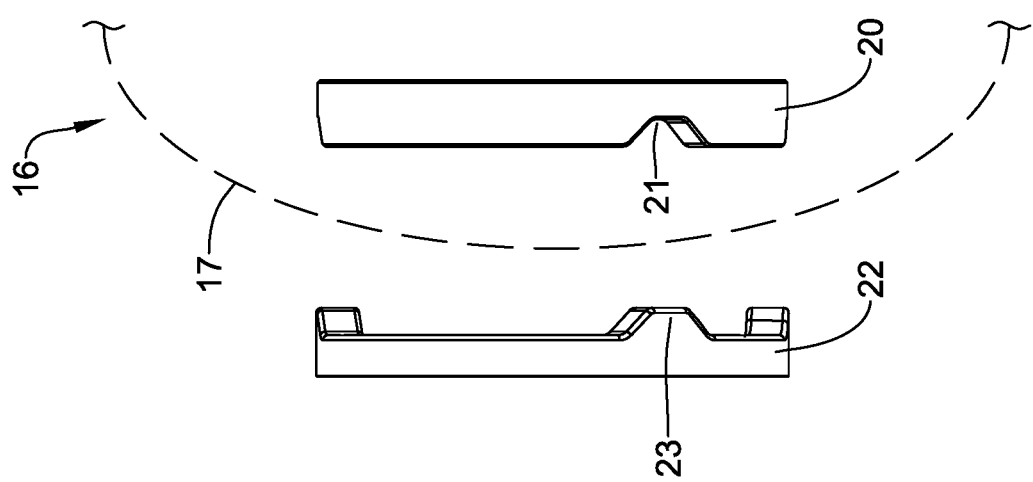

FIG. 2 is an exploded view of the connector assembly 16. Here it can be seen that the connector assembly includes a connector housing 18, an adapter or connector adapter 20 coupled to the connector housing 18, an end effector adapter 22 (e.g., which may be secured to the medical end effector 14), and an actuation mechanism 24. In some instances, the connector adapter 20 may also be referred to as a quick connect datum ring. In some of these and in other instances, the end effector adapter 22 may be referred to as the implement or tool guide datum ring. In some instances, a handle 26 may be coupled to the connector housing 18.

The connector adapter 20 may include one or more alignment regions 21. In some instances, the end effector adapter 22 may include one or more alignment members 23. In general, the alignment regions 21 and the alignment members 23 may help align the connector adapter 20 with the end effector adapter 22. More particularly, the shape the alignment regions 21 may correspond to and/or be configured to mate with alignment members 23 of the end effector adapter 22. In this example, the one or more alignment regions 21 may take the form of cutouts or grooves and the alignment members 23 may take the form of projections that correspond to the cutouts. In some instances, the alignment regions 21 and the alignment members 23 may function as kinematic constraints that constrain the assembly in all degrees of freedom and allow the end effector adapter 22 to be removed (e.g., be removed from the connector adapter 20) and replaced with a relatively tight spherical accuracy (e.g., within about 0.2 mm or less, or about 0.05 mm or less, or about 0.02 mm or less). In other words, the alignment regions 21 and alignment members 23 may help to form a kinematic coupling between the connector adapter 20 and the end effector adapter 22 with a high degree of positional repeatability while constraining the coupling in all degrees of freedom. The shapes of the alignment regions 21 and alignment members 23 may be such that, when misaligned, the regions 21 and members 23 are guided into proper alignment by continued force (e.g., because of one or more slopes, curves, or other shapes).

Moreover, given that the orientation can be controlled with a desired level of precision, additional orienting features (e.g., such as those for aligning a sterile barrier adapter) are not required. Indeed, the controlled orientation of the connector adapter 20 and the end effector adapter 22 allows for a sterile barrier or drape to be draped over suitable components without needing an adapter. This may aid in the maintaining sterility as well as obviate the need for a particular sterile barrier adapter with a particular orienting feature, which may simplify the process of connecting/disconnecting the connector adapter 20 and the end effector adapter 22. For illustration purposes, the sterile barrier 17 is shown schematically as being disposed between the connector adapter 20 and the end effector adapter 22. This may represent a suitable location for disposing the sterile barrier 17 during use.

The mechanism for actuating the connector assembly 16 is depicted in FIGS. 3-8. In these view, portions of the connector assembly 16 may be removed to make it easier to see various components of the connector assembly 16.

Figure 3:
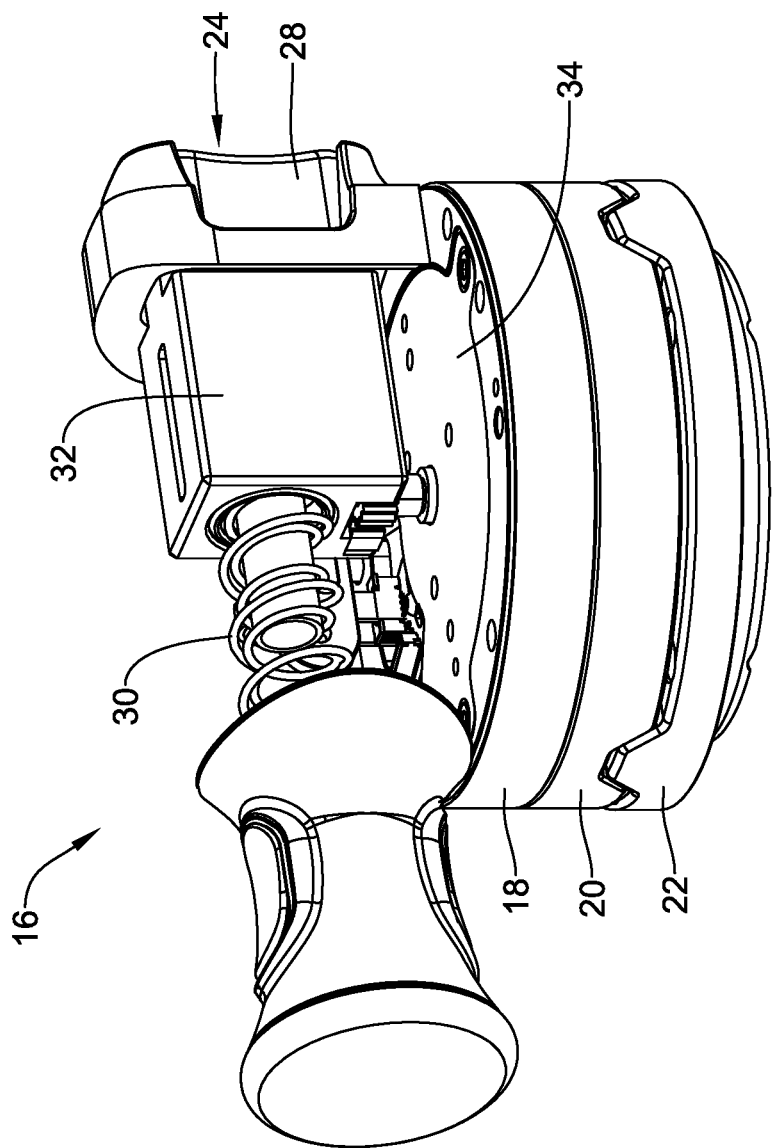
FIG. 3 is a partially cutaway view of a portion of an example connector assembly.

In FIG. 3, which is a partially cutaway view of the connector assembly 16, it can be seen that the actuation mechanism 24 may include an actuator 28. In this example, the actuator 28 takes the form of a depressible button. Other actuators are contemplated such as pull buttons, levers, knobs, twists, sliders, etc. A spring 30 may be coupled to the button 28. Other energy sources may be utilized instead of or in addition to the spring 30 such as a pneumatic member, a hydraulic member, a motor, combinations thereof, and/or the like. The spring 30 may exert a force on the button 28, essentially biasing the button 28 toward an "unpressed" position. In other words, when the button 28 is pressed, the button 28 exerts a compressive force on the spring 30. When the button 28 is released, the spring 30 exerts a force back onto the button 28 (e.g., via spring shifts from a compressed configuration to a relaxed, expanded configuration), causing the button 28 to move back to the original "unpressed" position.

Figure 4:
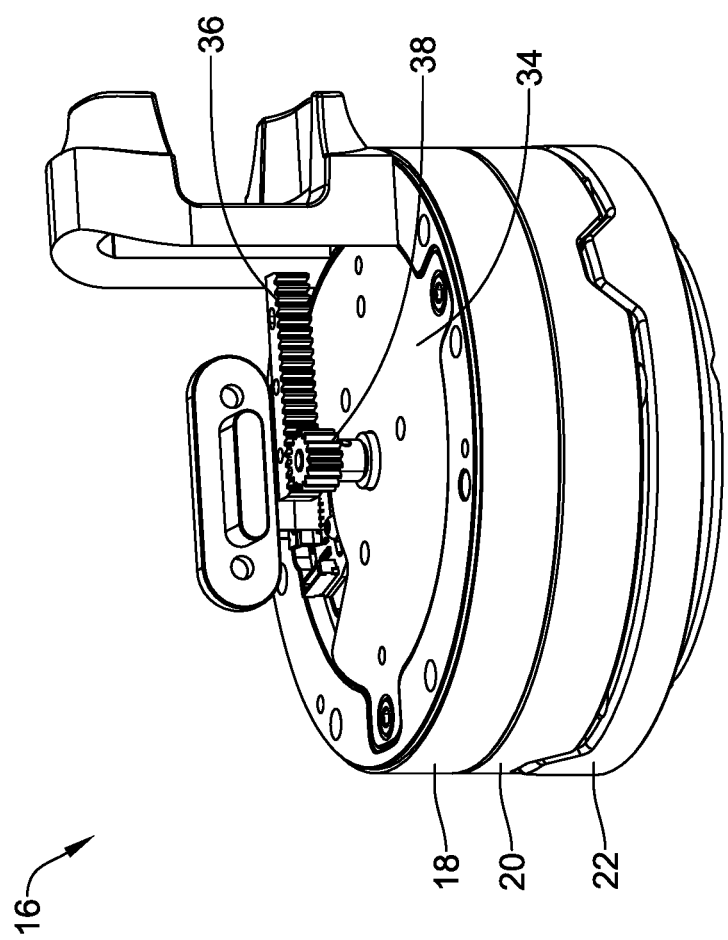
FIG. 4 is a partially cutaway view of a portion of an example connector assembly.
Figure 5:
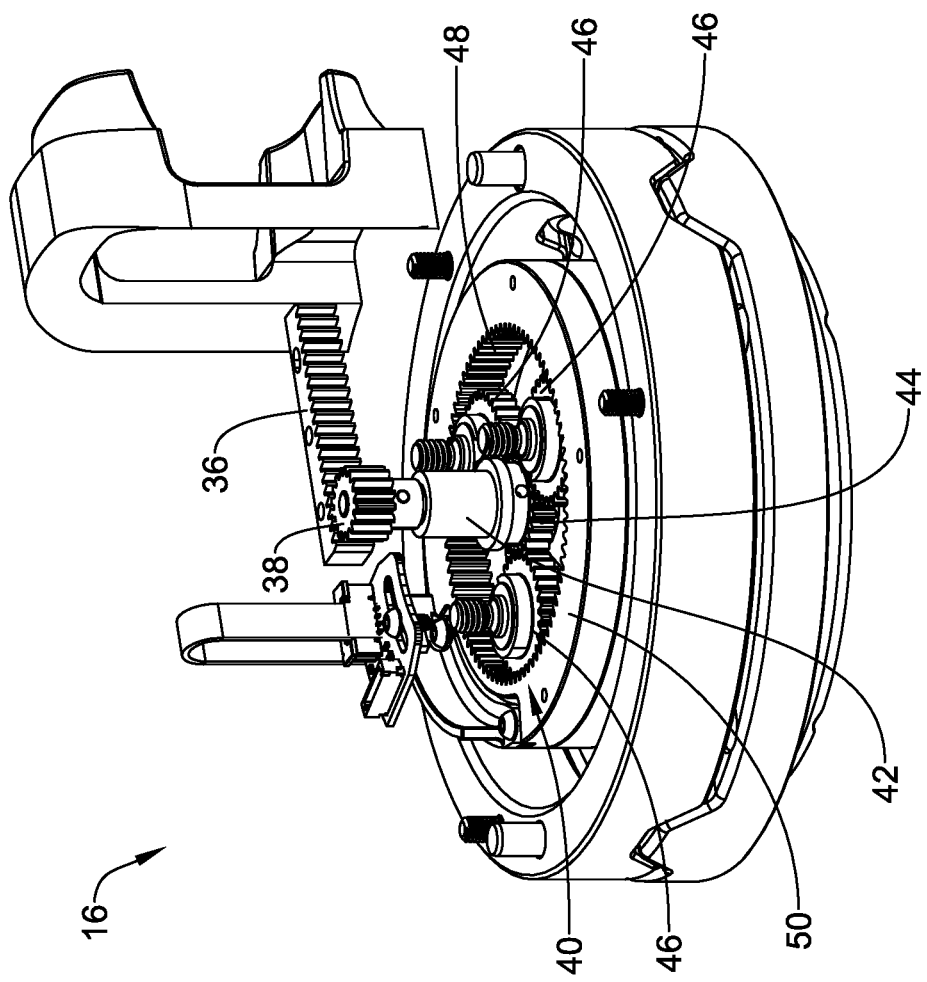
FIG. 5 is a partially cutaway view of a portion of an example connector assembly.

The button 28 may include a sidewall or housing 32. When the button 28 and housing 32 are removed (e.g., as shown in FIG. 4), it can be seen that the actuation mechanism 24 includes a rack 36 coupled to the button 28. In at least some instances, moving and/or pressing the button 28 shifts/moves the rack 36. The rack 36 may be engaged with a pinion 38. As shown in FIG. 3, the connector housing 18 may include a top plate 34. When the top plate 34 is removed (e.g., as shown in FIG. 5), it can be seen that the pinion 38 is coupled to and/or otherwise a component of a gearbox 40. Here it can be seen that the pinion 38 is coupled to a shaft 42 that extends to a drive gear 44 within the gearbox 40. The drive gear 44 engages a plurality of gear train rotating gears 46. The gear train rotating gears 46 engage a toothed or geared region 48 of a gearbox ring or gear train ring 50.

Collectively as shown in FIGS. 3-5, actuating/pressing the button 28 causes the rack 36 to shift/move. Because the rack 36 may be engaged with the pinion 38, movement of the rack 36 causes the pinion 38 to rotate. Rotation of the pinion 38 causes the drive gear 44 to rotate, which in turn rotates the gear train rotating gears 46. Because the geared region 48 of the gear train ring 50 is engaged with the gear train rotating gears 46, the rotation of the gear train rotating gears 46 causes the gear train ring 50 to rotate.

Figure 6:
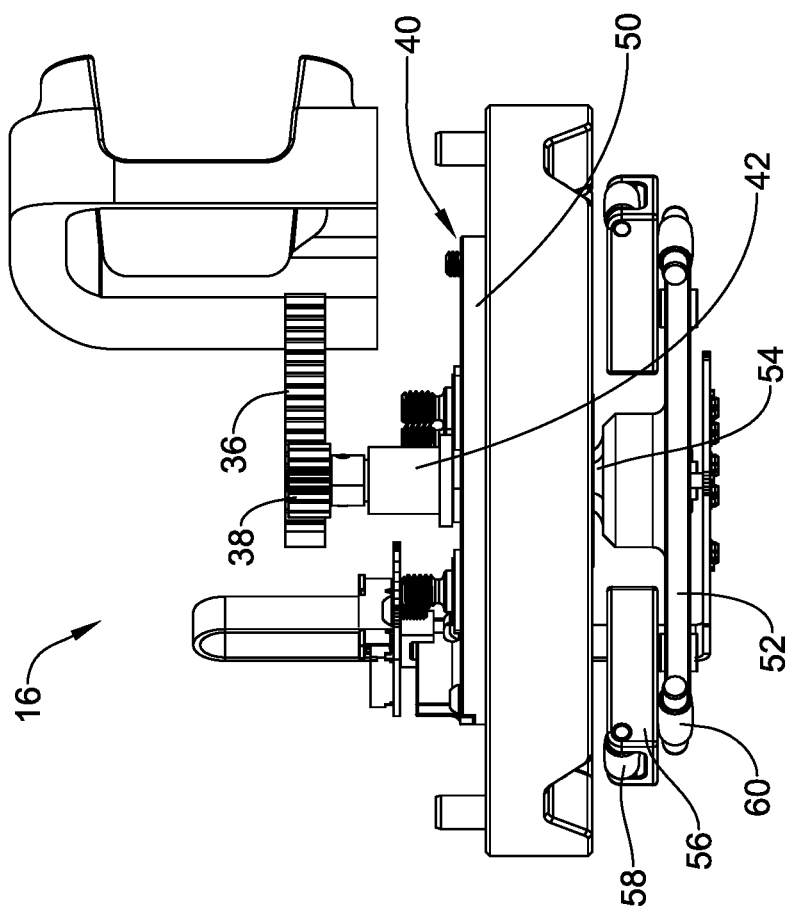
FIG. 6 is a partially cutaway view of a portion of an example connector assembly.
Figure 7:
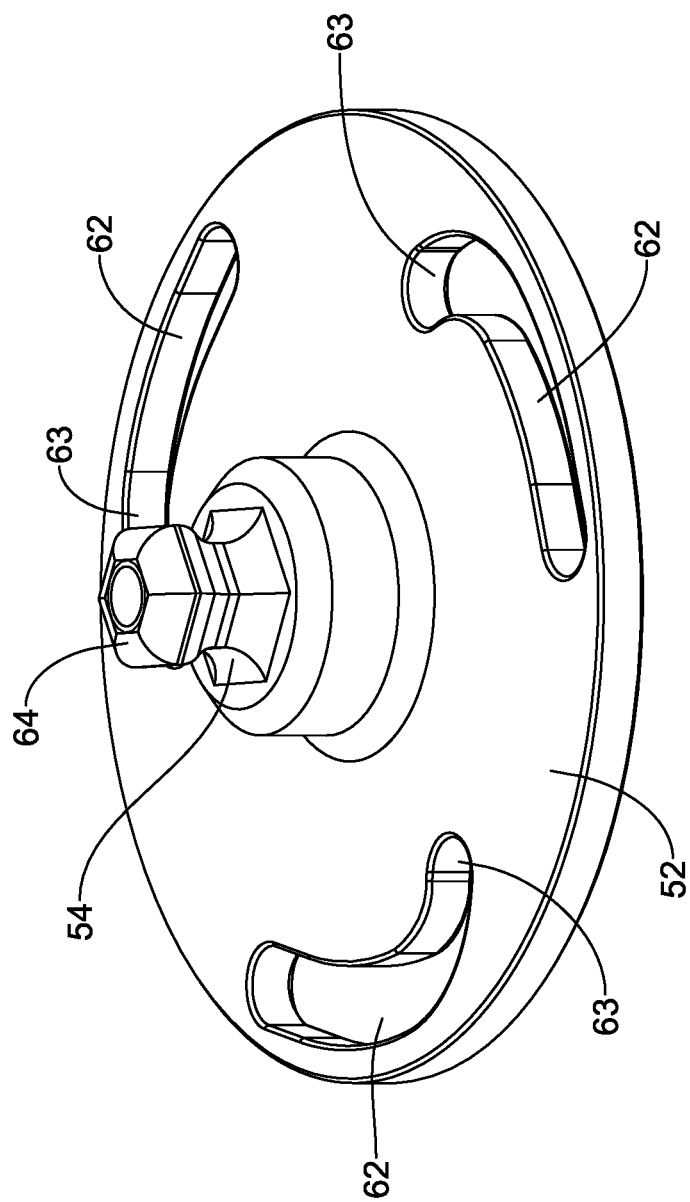
FIG. 7 is a perspective view of a portion of an example connector assembly.
Figure 7A:
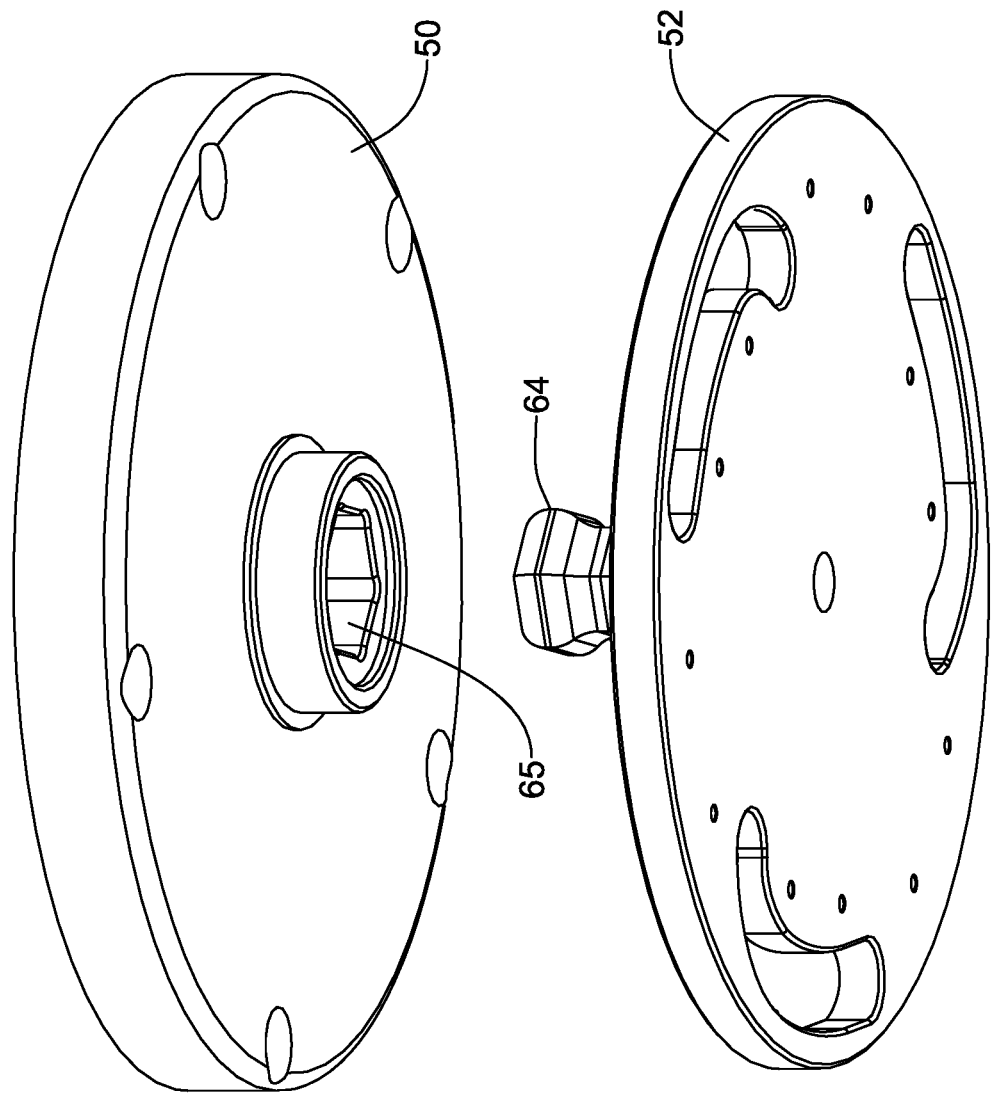
FIG. 7A is a perspective view of a portion of an example connector assembly.

Turning now to FIG. 6, here it can be seen that the gear train ring 50 is coupled to a cam member or plate 52. More particularly, the cam member 52 may include a cam shaft 54 that extends toward and secures to the gear train ring 50. The cam member 52 is shown in FIG. 7. Here it can be seen that the cam member 52 may include a plurality of cutouts 62. The cutouts 62 may have a curved or arcuate shape with an arcuate end region 63 that curves radially inward along the cam member 52. In some instances, the cutouts 62 may be described as having a boomerang shape. The cam shaft 54 may have a head or gear train engaging member 64. The gear train engaging member 64 may have a geometric end region with a rounded surface. The shape of the gear train engaging member 64 may be desirable for a number of reasons. For example, the geometric shape (e.g., in this example the gear train engaging member 64 has a hexagonal shape) allows the gear train engaging member 64 to engage the gear train ring 50 (e.g., a socket 65 disposed on the gear train ring 50 as shown in FIG. 7A) in a precise manner that results in efficient transfer of motion from the gear train ring 50 to the gear train engaging member 64. In other words, the shape of the gear train engaging member 64 is able to securely engage the gear train ring 50 so that rotation of the gear train ring 50 is efficiently transferred to the gear train engaging member 64. In addition, the rounded shape of the gear train engaging member 64 allows for cam member 52 to pivot relative to the gear train ring 50 while still maintaining connection. Thus, even if the cam member 52 experiences some pivoting while the connector adapter 20 is brought into engagement with the end effector adapter 22, efficient transfer of rotatory motion can still be accomplished between the gear train ring 50 and the cam member 52.

Referring back to FIG. 6, a plurality of linkages 56 may be coupled to the cam member 52. Each of the linkages 56 may include a roller 58, for example disposed adjacent to an end region thereof. A plurality of secondary rollers 60 may be coupled to the cam member 52. The rollers 58 and/or the secondary rollers 60 may help to increase the mechanical efficiency, reduce friction, and/or otherwise facilitate engagement of the linkages 56 with the end effector adapter 22 (e.g., as described in more detail below). In addition, the rollers 58 and/or the secondary rollers 60 may help to reduce damage to the sterile barrier 17 (e.g., as shown in FIGS. 1-2) when bringing the connector adapter 20 into engagement with the end effector adapter 22 and/or when actuating the linkages 56. For example, friction or sharp edges may risk the linkages 56 tearing or otherwise undesirably breaching the sterile barrier. In other implementations, other anti-friction or anti-tear designs can be used, such as applying anti-friction coatings or surface treatments to the linkages 56.

Figure 8:
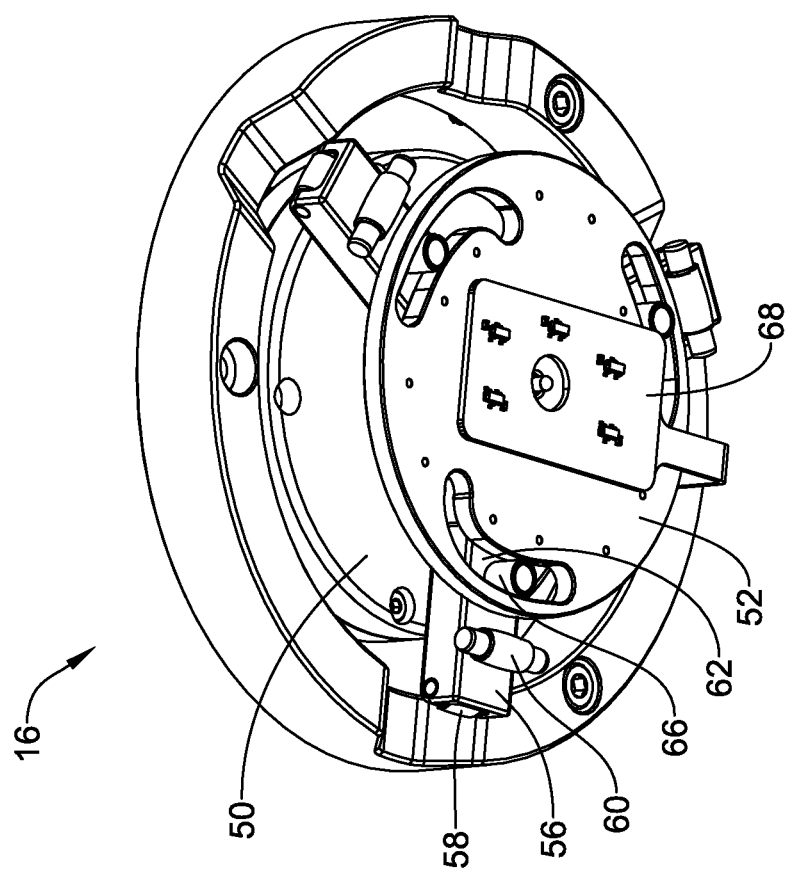
FIG. 8 is a partially cutaway view of a portion of an example connector assembly.

In some instances, a sensor 68 may be coupled to the cam member 52 as shown in FIG. 8. In some instances, the sensor may take the form of a magnetic field sensor (e.g., a Hall effect sensor). The sensor 68 and/or other sensors along the connector assembly 16 may be configured to sense a number of events such as when the connector adapter 20 is secured to the end effector adapter 22, when a tool is inserted into the medical end effector 14 (e.g., when a tool is inserted into the tool holder), the state/position of the linkages 56, combinations thereof, and/or the like.

Figure 9:
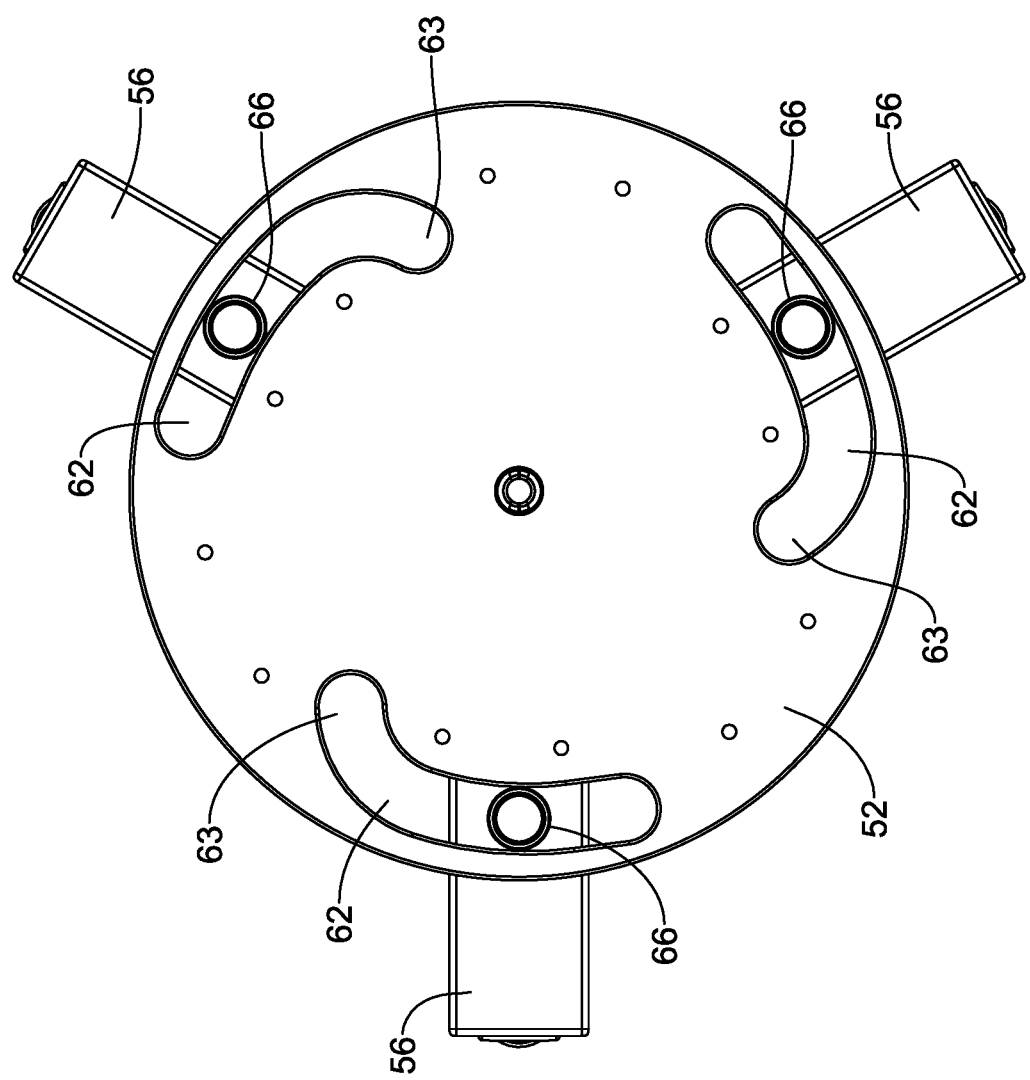
FIG. 9 depicts example linkages in a first configuration.
Figure 10:
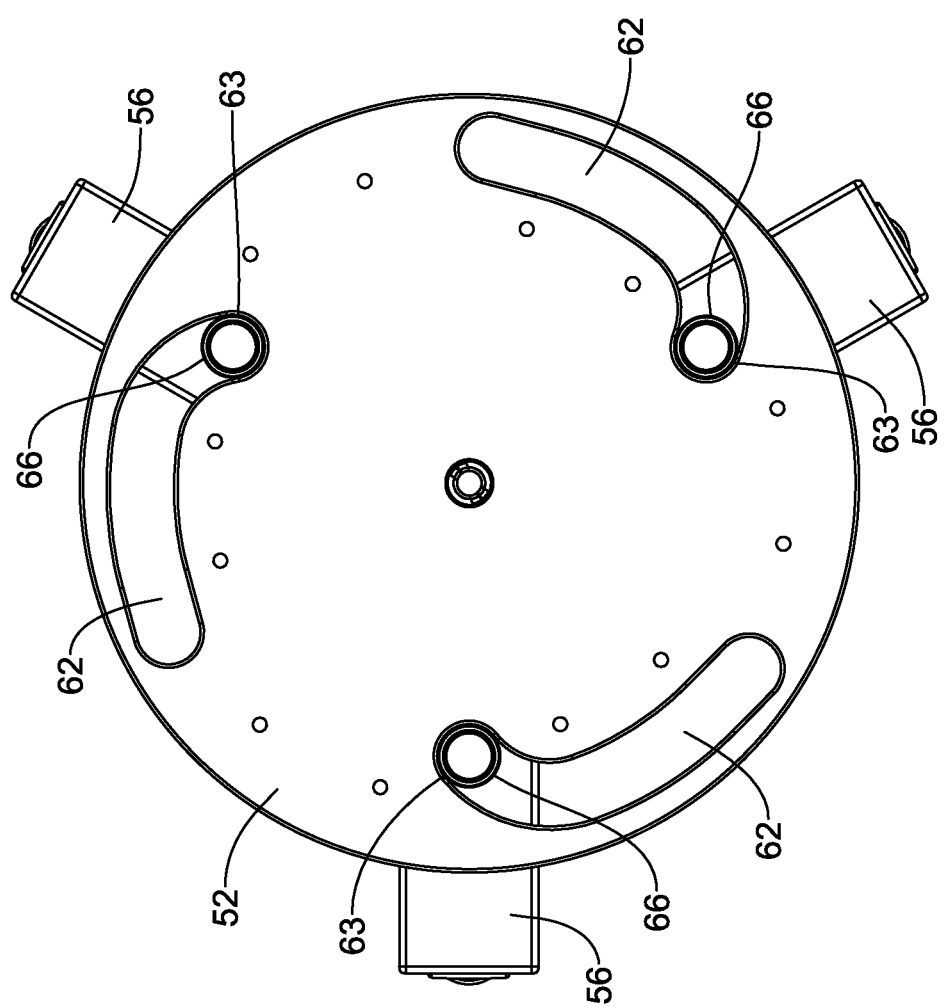
FIG. 10 depicts example linkages in a second configuration.

As can also be seen in FIG. 8, a shaft 66 is coupled to each of the linkages 56 that extends into (e.g., through) the cutouts 62 in the cam member 52. The shafts 66 are configured to travel within the cutouts 62 when the cam member 52 is rotated. In turn, this causes the linkages 56 to shift outward (e.g., as depicted in FIG. 9) or inward (e.g., as depicted in FIG. 10) when the cam member 52 is rotated. Shifting may be facilitated by the shape of the cutouts 62. For example, when the shafts 66 are disposed at a position that is spaced from the arcuate end region 63 of the cutouts 62 (e.g., as depicted in FIG. 9), the linkages 56 may be described as being in a first or locked position. When the cam member 52 is rotated, the shafts 66 may shift to the arcuate end region 63 of the cutouts 62 (e.g., as depicted in FIG. 10) and be described as being in a second or unlocked position. In general, when the linkages 56 are in the locked position, the linkages 56 engage the end effector adapter 22, which secures the connector adapter to the end effector adapter 22 as described in more detail herein. Shifting the linkages 56 between positions may be accomplished by rotating the cam member 52. Because the cam member 52 is coupled to the gear train ring 50 via the gear train engaging member 64 of the cam shaft 54, rotation of the gear train ring 50 causes rotation of the cam member 52 and, thus, shifting of the linkages 56 between the locked/unlocked positions.

In some instances, the linkages 56 may be in the locked position when the button 28 is in the "unpressed" position. As described herein, pressing the button 28 causes the gear train ring 50 to rotate, which causes the cam member 52 to rotate, which urges the shafts 66 toward the arcuate end region of the cutouts 62 in the cam member 52. This shifts the linkages 56 to the unlocked position. When the linkages 56 are in the unlocked position, the medical end effector 14 can be moved toward or away from the robotic arm 12. If it is desired to secure the medical end effector 14 to the robotic arm 12, the end effector adapter 22 can be brought into engagement with the connector adapter 20 (e.g., while the button is pressed), and, when suitably engaged, the button can be released to shift the linkages 56 to the locked configuration, thereby securing the medical end effector 14 to the robotic arm 12. In other instances, the linkages 56 may be in the locked position when the button 28 is in the pressed or in the "pressed" position.

Figure 11:
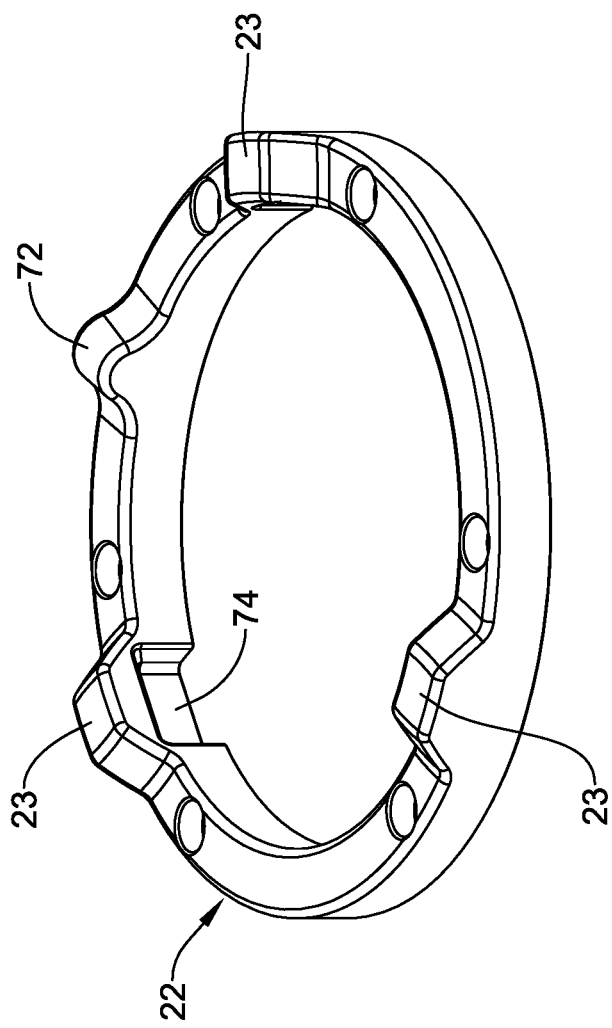
FIG. 11 is a perspective view of a portion of an example connector assembly.

FIG. 11 illustrates the end effector adapter 22. Here the alignment members 23 can be seen. In some instances, the alignment members 23 may have domed or rounded top and/or side surfaces. The alignment members 23 may be equally or unequally spaced about the end effector adapter 22. In some instances, the end effector adapter 22 may include a locating projection 72. The alignment members 23 and the locating projection 72 may engage or otherwise mate with corresponding region (e.g., alignment regions 21) of the connector adapter 20. As also can be seen in FIG. 11, the end effector adapter 22 may include a plurality of sockets 74. The sockets 74 are configured to engage and secure the linkages 56 when the linkages 56 are in the locked configuration.

U.S. patent application Ser. No. 17/400,888, filed Aug. 12, 2021, is herein incorporated by reference in its entirety for any and all purposes.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The detailed description should be read with reference to the drawings in which similar elements in different drawings are numbered the same. The drawings, which are not necessarily to scale, depict illustrative embodiments and are not intended to limit the scope of the invention.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An apparatus for connecting a robotic arm with a medical end effector, the apparatus comprising:
    a connector housing;
    an actuation mechanism disposed within the connector housing, the actuation mechanism including a plurality of linkage members and a gear assembly coupled to the plurality of linkage members;
    wherein each of the plurality of linkage members are configured to shift between a locked configuration and an unlocked configuration;
    wherein at least one of the plurality of linkage members includes a first linkage member having an end region;
    wherein a roller member is disposed adjacent to the end region of the first linkage member;
    an actuator coupled to the actuation mechanism, the actuator being configured to shift the plurality of linkage members between the locked configuration and the unlocked configuration;
    wherein the actuator includes a button coupled to a rack; and
    an adapter coupled to the connector housing, the adapter including a plurality of alignment regions.

2. The apparatus of claim 1, further comprising a sensor disposed adjacent to the connector housing.

3. The apparatus of claim 1, wherein the gear assembly includes a pinion engaged with the rack.

4. The apparatus of claim 3, wherein the pinion is coupled to a drive gear.

5. The apparatus of claim 4, wherein the drive gear is coupled to one or more gear train rotating gears.

6. The apparatus of claim 5, wherein the one or more gear train rotating gears are coupled to a geared region of a gear train.

7. The apparatus of claim 6, further comprising a cam plate having a gear train engaging member coupled to the gear train.

8. The apparatus of claim 7, wherein the gear train engaging member is configured to allow the cam plate to pivot relative to the gear train.

9. The apparatus of claim 7, wherein the gear train engaging member includes a geometric end region with a rounded surface.

10. The apparatus of claim 1, wherein the connector housing is configured to be coupled to a robotic arm.

11. The apparatus of claim 10, wherein the adapter is configured to be coupled to an end effector adapter.

12. The apparatus of claim 11, wherein the end effector adapter is coupled to the medical end effector.

13. The apparatus of claim 11, wherein the end effector adapter includes a plurality of alignment members configured to engage the alignment regions of the adapter.

14. The apparatus of claim 11, wherein the end effector adapter includes a plurality of linkage receiving regions configured to house the plurality of linkage members when the plurality of linkage members are in the locked configuration.

15. The apparatus of claim 11, further comprising a sterile barrier member disposed between the adapter and the end effector adapter.

* * * * *